(12) United States Patent
Gabriel et al.

(10) Patent No.: US 9,044,270 B2
(45) Date of Patent: Jun. 2, 2015

(54) APPARATUS FOR CONTROLLING A LOAD ON A HIP JOINT

(75) Inventors: Stefan Gabriel, Mattapoisett, MA (US); Mary O'Connell, Menlo Park, CA (US); Anton G. Clifford, Mountain View, CA (US); David Lowe, Redwood City, CA (US); Michael E. Landry, Austin, TX (US)

(73) Assignee: MOXIMED, INC., Hayward, CA (US)

( * ) Notice: Subject to any disclaimer, the term of this patent is extended or adjusted under 35 U.S.C. 154(b) by 403 days.

(21) Appl. No.: 13/075,012

(22) Filed: Mar. 29, 2011

(65) Prior Publication Data

US 2012/0253414 A1    Oct. 4, 2012

(51) Int. Cl.
*A61B 17/56* (2006.01)
*A61F 2/08* (2006.01)
*A61F 2/32* (2006.01)

(52) U.S. Cl.
CPC ............. *A61B 17/562* (2013.01); *A61F 2/32* (2013.01); *A61B 2017/567* (2013.01)

(58) Field of Classification Search
CPC ........... A61B 17/6425; A61B 17/7026; A61B 17/7028; A61B 17/7029; A61B 17/7064; A61B 17/8004; A61B 17/8061; A61B 2017/567
USPC .......................................... 623/23.39–23.41
See application file for complete search history.

(56) References Cited

U.S. PATENT DOCUMENTS

| | | | |
|---|---|---|---|
| 2,632,440 A | 3/1953 | Hauser | |
| 2,877,033 A | 3/1959 | Koetke | |
| 3,242,922 A | 3/1966 | Thomas | |
| 3,648,294 A | 3/1972 | Shahrestani | |
| 3,681,786 A | 8/1972 | Lynch | |
| 3,779,654 A | 12/1973 | Horne | |
| 3,875,594 A | 4/1975 | Swanson | |
| 3,902,482 A | 9/1975 | Taylor | |
| 3,988,783 A | 11/1976 | Treace | |
| 4,054,955 A * | 10/1977 | Seppo | 623/19.13 |
| 4,187,841 A | 2/1980 | Knutson | |
| 4,246,660 A | 1/1981 | Wevers | |
| 4,308,863 A | 1/1982 | Fischer | |
| 4,353,361 A | 10/1982 | Foster | |
| 4,501,266 A | 2/1985 | McDaniel | |
| 4,570,625 A | 2/1986 | Harris | |
| 4,576,158 A | 3/1986 | Boland | |

(Continued)

FOREIGN PATENT DOCUMENTS

| | | |
|---|---|---|
| CA | 1205602 | 6/1986 |
| DE | 19855254 | 6/2000 |

(Continued)

OTHER PUBLICATIONS

Larionov d. Yu, et al., "Medical Devices", Scientific and Technical Bimonthly Journal, May-Jun. 2008.

(Continued)

*Primary Examiner* — Christian Sevilla
*Assistant Examiner* — Eric S Gibson
(74) *Attorney, Agent, or Firm* — Adam J. Cermak; Cermak Nakajima & McGowan LLP

(57) ABSTRACT

An apparatus and related method for controlling a load on a human hip joint during normal gait while preserving motion. The approach is intended to treat osteoarthritis of the hip without substantially resisting an angular displacement associated with full mobility of the pelvis and femur bones.

16 Claims, 10 Drawing Sheets

(56) References Cited

U.S. PATENT DOCUMENTS

| | | | |
|---|---|---|---|
| 4,621,627 A | 11/1986 | DeBastiani et al. | |
| 4,637,382 A | 1/1987 | Walker | |
| 4,696,293 A | 9/1987 | Ciullo | |
| 4,759,765 A | 7/1988 | Van Kampen | |
| 4,776,851 A | 10/1988 | Bruchman et al. | |
| 4,846,842 A | 7/1989 | Connolly et al. | |
| 4,871,367 A | 10/1989 | Christensen et al. | |
| 4,923,471 A | 5/1990 | Morgan | |
| 4,942,875 A | 7/1990 | Hlavacek et al. | |
| 4,959,065 A | 9/1990 | Arnett et al. | |
| 4,988,349 A | 1/1991 | Pennig | |
| 5,002,574 A | 3/1991 | May et al. | |
| 5,011,497 A * | 4/1991 | Persson et al. | 623/23.41 |
| 5,019,077 A | 5/1991 | De Bastiani et al. | |
| 5,026,372 A | 6/1991 | Sturtzkopf et al. | |
| 5,041,112 A | 8/1991 | Mingozzi et al. | |
| 5,100,403 A | 3/1992 | Hotchkiss et al. | |
| 5,103,811 A | 4/1992 | Crupi | |
| 5,121,742 A | 6/1992 | Engen | |
| 5,152,280 A | 10/1992 | Danieli | |
| 5,318,567 A | 6/1994 | Vichard | |
| 5,352,190 A | 10/1994 | Fischer | |
| 5,375,823 A | 12/1994 | Navas | |
| 5,389,107 A | 2/1995 | Nassar et al. | |
| 5,405,347 A | 4/1995 | Lee et al. | |
| 5,415,661 A | 5/1995 | Holmes | |
| 5,540,688 A | 7/1996 | Navas | |
| 5,575,819 A | 11/1996 | Amis | |
| 5,578,038 A | 11/1996 | Slocum | |
| 5,601,553 A | 2/1997 | Trebing et al. | |
| 5,624,440 A | 4/1997 | Huebner | |
| 5,662,648 A | 9/1997 | Faccioli et al. | |
| 5,662,650 A | 9/1997 | Bailey et al. | |
| 5,681,313 A | 10/1997 | Diez | |
| 5,695,496 A | 12/1997 | Orsak et al. | |
| 5,716,357 A | 2/1998 | Rogozinski | |
| 5,803,924 A | 9/1998 | Oni et al. | |
| 5,873,843 A | 2/1999 | Draper | |
| 5,928,234 A | 7/1999 | Manspeizer | |
| 5,976,125 A | 11/1999 | Graham | |
| 5,976,136 A | 11/1999 | Bailey et al. | |
| 5,993,449 A | 11/1999 | Schlapfer | |
| 6,036,691 A | 3/2000 | Richardson | |
| 6,113,637 A | 9/2000 | Gill et al. | |
| 6,139,550 A | 10/2000 | Michelson | |
| 6,162,223 A | 12/2000 | Orsak et al. | |
| 6,176,860 B1 | 1/2001 | Howard | |
| 6,193,225 B1 * | 2/2001 | Watanabe | 267/180 |
| 6,264,696 B1 | 7/2001 | Reigner et al. | |
| 6,277,124 B1 | 8/2001 | Haag | |
| 6,315,852 B1 | 11/2001 | Magrini et al. | |
| 6,355,037 B1 | 3/2002 | Crosslin et al. | |
| 6,364,881 B1 | 4/2002 | Apgar et al. | |
| 6,409,729 B1 | 6/2002 | Martinelli et al. | |
| 6,482,232 B1 | 11/2002 | Boucher et al. | |
| 6,494,914 B2 | 12/2002 | Brown et al. | |
| 6,527,733 B1 | 3/2003 | Ceriani et al. | |
| 6,540,708 B1 | 4/2003 | Manspeizer | |
| 6,572,653 B1 | 6/2003 | Simonson | |
| 6,599,322 B1 | 7/2003 | Amrich et al. | |
| 6,620,332 B2 | 9/2003 | Amrich | |
| 6,623,486 B1 | 9/2003 | Weaver | |
| 6,663,631 B2 | 12/2003 | Kuntz | |
| 6,692,497 B1 | 2/2004 | Pohjonen et al. | |
| 6,692,498 B1 | 2/2004 | Niiranen et al. | |
| 6,752,831 B2 | 6/2004 | Sybert et al. | |
| 6,884,242 B2 | 4/2005 | LeHuec et al. | |
| 6,966,910 B2 | 11/2005 | Ritland | |
| 6,972,020 B1 | 12/2005 | Grayson et al. | |
| 6,997,940 B2 | 2/2006 | Bonutti | |
| 7,018,418 B2 | 3/2006 | Amrich et al. | |
| 7,029,475 B2 | 4/2006 | Panjabi | |
| 7,128,744 B2 | 10/2006 | Weaver et al. | |
| 7,141,073 B2 | 11/2006 | May et al. | |
| 7,188,626 B2 | 3/2007 | Foley et al. | |
| 7,201,728 B2 | 4/2007 | Sterling | |
| 7,235,077 B1 | 6/2007 | Wang et al. | |
| 7,235,102 B2 | 6/2007 | Ferree et al. | |
| 7,238,203 B2 | 7/2007 | Bagga et al. | |
| 7,241,298 B2 | 7/2007 | Nemec et al. | |
| 7,247,157 B2 | 7/2007 | Prager et al. | |
| 7,252,670 B2 | 8/2007 | Morrison et al. | |
| 7,261,739 B2 | 8/2007 | Ralph et al. | |
| 7,273,481 B2 | 9/2007 | Lombardo et al. | |
| 7,276,070 B2 | 10/2007 | Muckler | |
| 7,282,065 B2 | 10/2007 | Kirschman | |
| 7,285,134 B2 | 10/2007 | Berry et al. | |
| 7,288,094 B2 | 10/2007 | Lindemann et al. | |
| 7,288,095 B2 | 10/2007 | Baynham et al. | |
| 7,291,150 B2 | 11/2007 | Graf | |
| 7,306,605 B2 | 12/2007 | Ross | |
| 7,322,983 B2 | 1/2008 | Harris | |
| 7,322,984 B2 | 1/2008 | Doubler et al. | |
| 7,341,589 B2 | 3/2008 | Weaver et al. | |
| 7,361,196 B2 | 4/2008 | Fallin et al. | |
| 7,621,962 B2 | 11/2009 | Lakin | |
| 8,088,166 B2 * | 1/2012 | Makower et al. | 623/20.14 |
| 2001/0020143 A1 | 9/2001 | Stark et al. | |
| 2002/0095154 A1 | 7/2002 | Atkinson et al. | |
| 2002/0151978 A1 | 10/2002 | Zacouto et al. | |
| 2003/0216809 A1 | 11/2003 | Ferguson | |
| 2004/0260302 A1 | 12/2004 | Manspeizer | |
| 2004/0267179 A1 | 12/2004 | Leman | |
| 2005/0049708 A1 | 3/2005 | Atkinson et al. | |
| 2005/0085815 A1 | 4/2005 | Harms et al. | |
| 2005/0119744 A1 | 6/2005 | Buskirk et al. | |
| 2005/0154390 A1 | 7/2005 | Biedermann et al. | |
| 2005/0192674 A1 | 9/2005 | Ferree | |
| 2005/0261680 A1 | 11/2005 | Draper | |
| 2006/0064169 A1 | 3/2006 | Ferree | |
| 2006/0085001 A1 | 4/2006 | Michelson | |
| 2006/0178744 A1 | 8/2006 | de Villiers et al. | |
| 2007/0043356 A1 | 2/2007 | Timm et al. | |
| 2007/0106299 A1 | 5/2007 | Manspeizer | |
| 2007/0161993 A1 | 7/2007 | Lowery et al. | |
| 2007/0168033 A1 | 7/2007 | Kim et al. | |
| 2007/0168036 A1 | 7/2007 | Ainsworth et al. | |
| 2007/0198088 A1 | 8/2007 | Biedermann et al. | |
| 2007/0198091 A1 | 8/2007 | Boyer et al. | |
| 2007/0244483 A9 | 10/2007 | Winslow et al. | |
| 2007/0244488 A1 | 10/2007 | Metzger et al. | |
| 2007/0288014 A1 | 12/2007 | Shadduck et al. | |
| 2008/0015591 A1 | 1/2008 | Castaneda et al. | |
| 2008/0015592 A1 | 1/2008 | Long et al. | |
| 2008/0015593 A1 | 1/2008 | Pfefferle et al. | |
| 2008/0071373 A1 | 3/2008 | Molz et al. | |
| 2008/0071375 A1 | 3/2008 | Carver et al. | |
| 2008/0097441 A1 | 4/2008 | Hayes et al. | |
| 2008/0132954 A1 | 6/2008 | Sekhon et al. | |
| 2008/0154378 A1 | 6/2008 | Pelo | |
| 2008/0275552 A1 * | 11/2008 | Makower et al. | 623/13.13 |
| 2008/0275555 A1 * | 11/2008 | Makower et al. | 623/14.12 |
| 2008/0275558 A1 * | 11/2008 | Clifford et al. | 623/20.14 |
| 2008/0275560 A1 | 11/2008 | Clifford et al. | |
| 2009/0318976 A1 * | 12/2009 | Gabriel et al. | 606/283 |
| 2010/0063549 A1 | 3/2010 | Orbay et al. | |
| 2010/0137996 A1 * | 6/2010 | Clifford et al. | 623/23.41 |
| 2012/0053644 A1 * | 3/2012 | Landry et al. | 606/86 R |
| 2012/0253414 A1 * | 10/2012 | Gabriel et al. | 606/86 R |

FOREIGN PATENT DOCUMENTS

| | | |
|---|---|---|
| EP | 0383419 | 8/1990 |
| EP | 0953317 | 4/1999 |
| EP | 1770302 | 4/2007 |
| EP | 1429675 | 10/2007 |
| EP | 1682020 | 10/2007 |
| EP | 1847228 | 10/2007 |
| EP | 1847229 | 10/2007 |
| EP | 1005290 | 2/2008 |
| EP | 1468655 | 5/2008 |
| GB | 1507953 | 4/1978 |
| GB | 2223406 | 4/1990 |
| GB | 2250919 | 5/1991 |

(56) References Cited

FOREIGN PATENT DOCUMENTS

| | | |
|---|---|---|
| GB | 2250919 | 10/1993 |
| JP | 59-131348 | 7/1984 |
| JP | 2532346 | 4/1995 |
| JP | 7100159 | 4/1995 |
| JP | 2000-503865 | 4/2000 |
| JP | 2001-145647 | 4/2000 |
| JP | 2003-102744 | 5/2001 |
| JP | 2006-280951 | 10/2006 |
| JP | 2007-167318 | 7/2007 |
| JP | 2007-167319 | 7/2007 |
| JP | 2007170969 | 7/2007 |
| RU | 1769868 | 10/1992 |
| RU | 2085148 | 7/1997 |
| RU | 2217105 | 11/2003 |
| RU | 2241400 | 9/2004 |
| SU | 578063 | 11/1977 |
| SU | 578957 | 11/1977 |
| SU | 624613 | 8/1978 |
| SU | 640740 | 1/1979 |
| SU | 704605 | 12/1979 |
| SU | 719612 | 3/1980 |
| SU | 741872 | 7/1980 |
| SU | 1186204 | 10/1985 |
| SU | 1251889 | 8/1986 |
| SU | 1316666 | 6/1987 |
| SU | 1588404 | 8/1990 |
| SU | 1699441 | 12/1991 |
| WO | WO9107137 | 5/1991 |
| WO | WO94/06364 | 3/1994 |
| WO | WO96/19944 | 7/1996 |
| WO | WO2004/019831 | 3/2004 |
| WO | WO2004/024037 | 3/2004 |
| WO | WO2007/056645 | 5/2005 |
| WO | WO2006045091 | 4/2006 |
| WO | WO2006049993 | 5/2006 |
| WO | WO2006/110578 | 10/2006 |
| WO | WO2007/090009 | 8/2007 |
| WO | WO2007/090015 | 8/2007 |
| WO | WO2007/090017 | 8/2007 |
| WO | WO2007106962 | 9/2007 |
| WO | WO2007109417 | 9/2007 |
| WO | WO2007109436 | 9/2007 |
| WO | WO2007114769 | 10/2007 |
| WO | WO2007117571 | 10/2007 |
| WO | WO2008006098 | 1/2008 |
| WO | WO2008137487 | 11/2008 |

OTHER PUBLICATIONS

Lapinskaya, V.S., et al., "An Endoapparatus for Restoration of the Hip Joint", Writers Collective, 2008, UDK 615.472.03:616,728.2-089.28.
Lapinskaya, Valentina Spiridovna, "Treatment of Diseases and Injuries of Hip Joint Using a Method of Distractions", Kuibyshev Medial Institute, 1990.
Nagai, et al., "B109 Mobility Evaluation of Hip-Joint Nonweight-Bearing Device", The Japan Society of Mechanical Engineers No. 02-26.
Tomita, Naohide, "Development of Treatment Devices for Cartilage Regeneration", BME vol. 16, No. 2.
Lentsner, A.A., et al., "Device for Functional Relief of Hip Joint in Cotyloid Cavity Fracture Cases", Ortop Travmatol Protez. Apr. 1990 (4) 44-6.
Wilke, hans-Joachim et al., "Biomechanical Evaluation of a New Total Posterior-Element Replacement System"; Spine, 2006, vol. 31, No. 24, pp. 2790-2796.
Wilkins, Ross M., M.D. et al.; "The Phenix Expandable Prosthesis"; Clinical Orthopaedics and Related Research, No. 382, pp. 51-58.
Yamamoto, Ei et al.; "Effects of Stress Shielding on the Transverse Mechanical Properties of Rabbit Patellar Tendons"; Journal of Biomechanical Engineering, 2000, vol. 122, pp. 608-614.
Aldegheri, Roberto, M.D. et al.; "Articulated Distraction of the Hip—Conservative Surgery for Arthritis in Young Patients", Clinical Orthopaedics and Related Research, No. 301, pp. 94-101.

Benzel, Edward; "Qualititive Attributes of Spinal Implants"; in: Biomechanics of Spine Stabilization, 1995.
Buckwalter, Joseph A,: "Joint distraction for osteoarthritis"; The Lancet, Department of Orthopaedic Surgery, University of Iowa Hospitals and Clinics, vol. 347, Feb. 3, 1996, pp. 279-280.
Coathup, M.J. et al.; "Osseo-mechanical induction of extro-cortiacal plates with references to their surfact properties and goemoetic designs", Elsevier, Biomaterials 20 (1999) 793-800.
Deie, Masataka, M.D. et al.; "A new Articulated Distraction Arthrosplasty Device for Treatment of the Osteoarthritic Knee Joint: A Preliminary Report"; Arthroscopy: The Journal of Arthoscopic and Related Surgery; vol. 23, No. 8 (Aug. 2007): pp. 833-838.
Dienst, M. et al.; "Dynamic external fixation for distal radius fractures"; Clinical Orthopaedics and Related Research, 1997, vol. 338, pp. 160-171.
Gunther, Klaus-Peter, M.D.; "Surgical approaches for osteoarthritis"; Best Practice and Research Clinical Rheumatology, vol. 15, No. 4, pp. 627-643, 2001.
Hall, J. et al.; "Use of a hinged external fixator for elbow instability after severe distal humeral fracture"; Journal of Orthopaedic Trauma, 2000, vol. 14, No. 6 pp. 442-448.
Klein, D. et al.; "Percutaneous treatment of carpal, metacarpal, and phalangeal injuries"; Clinical Orthopaedics and Related Research, 200, vol. 375, pp. 116-125.
Krakauer, J. et al.; "Hinged device for fractures involving the proximal interphalangeal joint"; Clinical Orthopaedics and Related Research, 1996, vol. 327, pp. 29-37.
Lafeber et al., Unloading Joints to Treat Osteoarthritis, Including Joint Distraction, Current Opinion in Rheumatology 2006, 18; 519-525.
Madey, S. et al; Hinged external fixation of the elbow: optimal axis alignment to minimize motion resistance; Journal of Orthopaedic Trauma, 2000, vol. 14, No. 1, pp. 41-47.
Neel, Michael D., M.D.; "Repiphysis—Limb Salvage System for the Skeletally Immature"; Wright Medical Techology, Repiphysis Limb Salvage System, 2001, pp. 1-8.
Neel, Michael D. M.D. et al.; "Early Multicenter Experience With a Noninvasive Expandable Prosthesis"; Clinical Orthopaedics and Related Research, 2003, No. 415, pp. 72-81.
Nockels, Russ P.; "Dynamic Stabilization in the Surgical Management of Painful Lumbar Spinal Disorders"; Spine, 2005, vol. 30, No. 16S, pp. S68-S72.
Perry, Clayton R. et al.; "Patellar Fixation Protected with a Load-Sharing Cable: A Mechanical and Clinical Study": Journal of Orthopaedic Trauma, 1988, vol. 2, No. 3, pp. 234-240.
Orthofix; "Xcaliber Articulated Ankle"; advertising brochure, May 2004.
Orthofix; "Gentle Limb Deformity Correction", website pages, http://www.eight-plate.com/, 2008.
Pilliar et al., Bone ingrowth and Stress Shielding with a Porous Surface Coated Fracture Fixation Plate, Journal of Biomedical Materials Research, vol. 13, 799-810 (1979).
Pollo, Fabian E. et al.; "Reduction of Medical Compartment Loads With Valgus Bracing of the Osteoarthritic Knee"; American Journal Sports Medicine, vol. 30, No. 3, 2002; pp. 414-421.
Repicci, John A., M.D. et al. "Minimally invasive unicondylar knee arthroplasty for the treatment of unicompartmental osteoarthritis: an outpatient bypass procedure"; Orthopaedic Clinics of North America, 35 (2004), pp. 201-216.
Sommerkamp, G. et al.; "Dynamic external fixation of unstable reatures of the distal part of the radius"; The Journal of Bone and Joint Surgery; 1994, vol. 76-A, No. 8, pp. 1149-1161.
Tencer, Allan F. et al. "Fixation of the Patell (Chap, 9.3)"; in: Biomechanics in Orthopedic Trauma Bone Fracture and Fixation, 1994.
Thakur, A.J.; "Tension Band Wiring"; in; The Elements of Fracture Fixation 1997.
Uchikura, C. et al.; "Comparative study of nonbridging and bridging external fixators for unstable distal radius fractures"; Journal of Orthopaedic Science, 2004, vol. 9, pp. 560-565.
Weisstein, Jason S., M.D. et al.; "Oncologic Approaches to Pediatric Limb Preservation"; Journal of the American Academy of Orthopaedic Surgeons; vol. 13, No. 8, Dec. 2005.

* cited by examiner

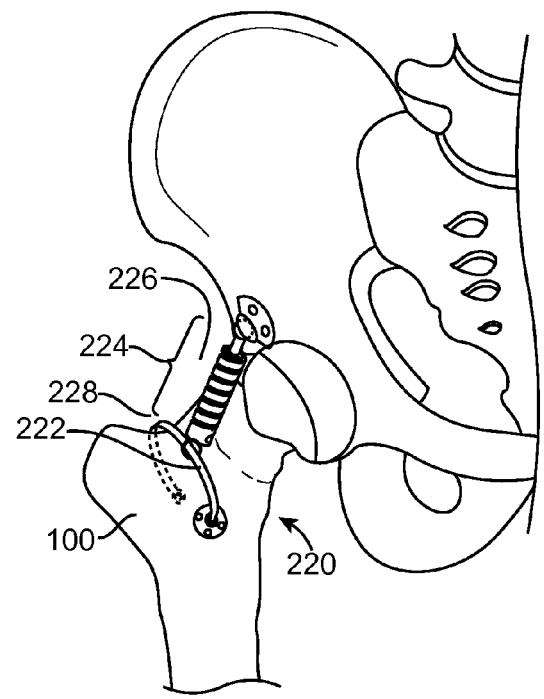
FIG. 11A
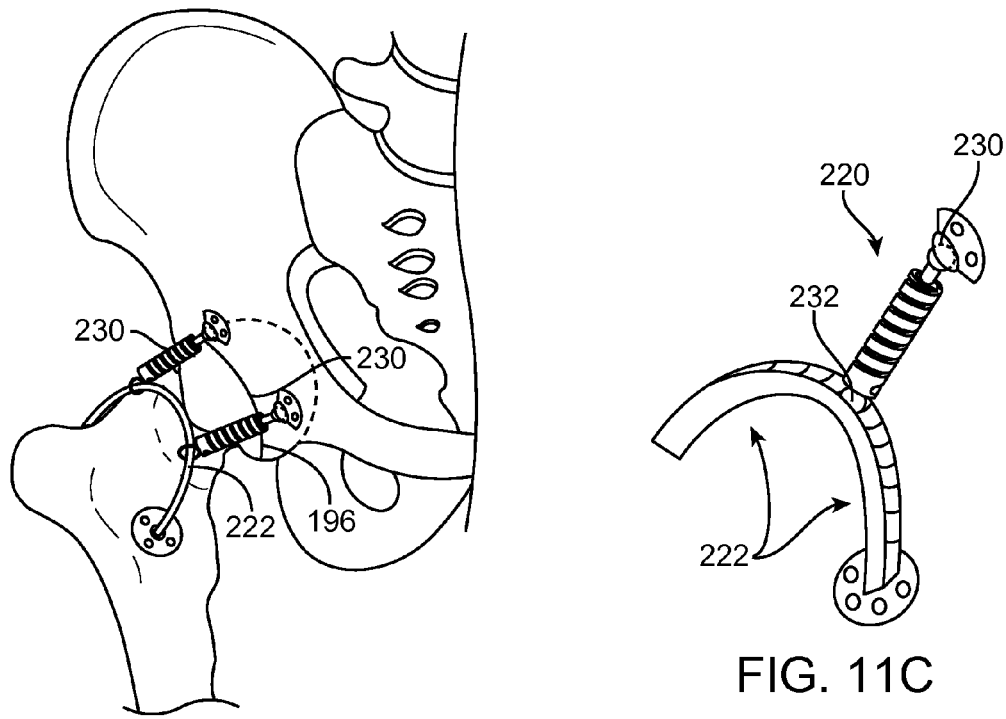
FIG. 11B
FIG. 11C

APPARATUS FOR CONTROLLING A LOAD ON A HIP JOINT

BACKGROUND

The present disclosure is directed toward apparatus and methods for treating joints and in particular, to treating hip joints affected with osteoarthritis.

A joint is the location at which two or more bones make contact. Joints are constructed to allow movement and provide mechanical support, and are classified structurally and functionally. Structural classification is determined by how the bones connected to each other, while functional classification is determined by the degree of movement between the articulating bones. In practice, there is significant overlap between the two types of classifications.

There are three structural classifications of joints, namely fibrous or immovable joints, cartilaginous joints and synovial joints. Fibrous/Immovable bones are connected by dense connective tissue, consisting mainly of collagen. The fibrous joints are further divided into three types:
  sutures which are found between bones of the skull;
  syndesmosis which are found between long bones of the body; and
  gomphosis which is a joint between the root of a tooth and the sockets in the maxilla or mandible.

Cartilaginous bones are connected entirely by cartilage (also known as "synchondroses"). Cartilaginous joints allow more movement between bones than a fibrous joint but less than the highly mobile synovial joint. Cartilaginous joints include the artificial discs of the spine.

Synovial joints have a space between the articulating bones for synovial fluid. This classification contains joints that are the most mobile of the three, and includes the hip, knee and shoulder. These are further classified into ball and socket joints, condyloid joints, saddle joints, hinge joints, pivot joints, and gliding joints.

Joints can also be classified functionally, by the degree of mobility they allow. Synarthrosis joints permit little or no mobility. They can be categorized by how the two bones are joined together. That is, synchrondoses are joints where the two bones are connected by a piece of cartilage. Synostoses are where two bones that are initially separated eventually fuse together as a child approaches adulthood. By contrast, amphiarthrosis joints permit slight mobility. The two bone surfaces at the joint are both covered in hyaline cartilage and joined by strands of fibrocartilage. Most amphiarthrosis joints are cartilaginous.

Finally, diarthrosis joints permit a variety of movements (e.g. flexion, adduction, pronation). Only synovial joints are diarthrodial and they can be divided into six classes: 1. ball and socket—such as the shoulder or the hip and femur; 2. hinge—such as the elbow; 3. pivot—such as the radius and ulna; 4. condyloidal (or ellipsoidal)—such as the wrist between radius and carps, or knee; 5. saddle—such as the joint between carpal thumbs and metacarpals; and 6. gliding—such as between the carpals.

Synovial joints (or diarthrosis, or diarthroidal joints) are the most common and most moveable type of joints in the body. As with all other joints in the body, synovial joints achieve movement at the point of contact of the articulating bones. Structural and functional differences distinguish the synovial joints from the two other types of joints in the body, with the main structural difference being the existence of a cavity between the articulating bones and the occupation of a fluid in that cavity which aids movement. The whole of a diarthrosis is contained by a ligamentous sac, the joint capsule or articular capsule. The surfaces of the two bones at the joint are covered in cartilage. The thickness of the cartilage varies with each joint, and sometimes may be of uneven thickness. Articular cartilage is multi-layered. A thin superficial layer provides a smooth surface for the two bones to slide against each other. Of all the layers, it has the highest concentration of collagen and the lowest concentration of proteoglycans, making it very resistant to shear stresses. Deeper than that is an intermediate layer, which is mechanically designed to absorb shocks and distribute the load efficiently. The deepest layer is highly calcified, and anchors the articular cartilage to the bone. In joints where the two surfaces do not fit snugly together, a meniscus or multiple folds of fibro-cartilage within the joint correct the fit, ensuring stability and the optimal distribution of load forces. The synovium is a membrane that covers all the non-cartilaginous surfaces within the joint capsule. It secretes synovial fluid into the joint, which nourishes and lubricates the articular cartilage. The synovium is separated from the capsule by a layer of cellular tissue that contains blood vessels and nerves.

Various maladies can affect the joints, one of which is arthritis. Arthritis is a group of conditions where there is damage caused to the joints of the body. Arthritis is the leading cause of disability in people over the age of 65.

There are many forms of arthritis, each of which has a different cause. Rheumatoid arthritis and psoriatic arthritis are autoimmune diseases in which the body is attacking itself. Septic arthritis is caused by joint infection. Gouty arthritis is caused by deposition of uric acid crystals in the joint that results in subsequent inflammation. The most common form of arthritis, osteoarthritis is also known as degenerative joint disease and occurs following trauma to the joint, following an infection of the joint or simply as a result of aging.

Unfortunately, all arthritides feature pain. Patterns of pain differ among the arthritides and the location. Rheumatoid arthritis is generally worse in the morning; in the early stages, patients often do not have symptoms following their morning shower.

Osteoarthritis (OA, also known as degenerative arthritis or degenerative joint disease, and sometimes referred to as "arthrosis" or "osteoarthrosis" or in more colloquial terms "wear and tear"), is a condition in which low-grade inflammation results in pain in the joints, caused by wearing of the cartilage that covers and acts as a cushion inside joints. As the bone surfaces become less well protected by cartilage, the patient experiences pain upon weight bearing, including walking and standing. Due to decreased movement because of the pain, regional muscles may atrophy, and ligaments may become more lax. OA is the most common form of arthritis.

The main symptoms of osteoarthritis is chronic pain, causing loss of mobility and often stiffness. "Pain" is generally described as a sharp ache, or a burning sensation in the associated muscles and tendons. OA can cause a crackling noise (called "crepitus") when the affected joint is moved or touched, and patients may experience muscle spasm and contractions in the tendons. Occasionally, the joints may also be filled with fluid. Humid weather increases the pain in many patients.

OA commonly affects the hand, feet, spine, and the large weight-bearing joints, such as the hips and knees, although in theory, any joint in the body can be affected. As OA progresses, the affected joints appear larger, are stiff and painful, and usually feel worse, the more they are used and loaded throughout the day, thus distinguishing it from rheumatoid arthritis. With progression in OA, cartilage looses its viscoelastic properties and it's ability to absorb load.

Generally speaking, the process of clinical detectable osteoarthritis is irreversible, and typical treatment consists of medication or other interventions that can reduce the pain of OA and thereby improve the function of the joint. According to an article entitled *Surgical Approaches for Osteoarthritis* by Klaus-Peter Günther, MD, over recent decades, a variety of surgical procedures have been developed with the aim of decreasing or eliminating pain and improving function in patients with advanced osteoarthritis (OA). The different approaches include preservation or restoration of articular surfaces, total joint replacement with artificial implants, and arthrodesis (fusion).

Arthrodesis are described as being reasonable alternatives for treating OA of small hand and foot joints as well as degenerative disorders of the spine, but were deemed to be rarely indicated in large weight-bearing joints such as the hip due to functional impairment of gait, cosmetic problems and further side-effects. Total joint replacement was characterized as an extremely effective treatment for severe joint disease. Moreover, recently developed joint-preserving treatment modalities were identified as having a potential to stimulate the formation of a new articular surface in the future. However, it was concluded that such techniques do not presently predictably restore a durable articular surface to an osteoarthritic joint. The correction of mechanical abnormalities by osteotomy and joint debridement are still considered as treatment options in many patients.

Joint replacement is one of the most common and successful operations in modern orthopaedic surgery. It consists of replacing painful, arthritic, worn or diseased parts of the joint with artificial surfaces shaped in such a way as to allow joint movement. Such procedures are a last resort treatment as they are highly invasive and require substantial periods of recovery. Joint replacement is sometimes called total joint replacement indicating that all joint surfaces are replaced. This contrasts with hemiarthroplasty (half arthroplasty) in which only one bone's joint surface is replaced and unincompartmental arthroplasty in which both surfaces of the knee, for example, are replaced but only on the inner or outer sides, not both. Thus, arthroplasty as a general term, is an operative procedure of orthopaedic surgery performed, in which the arthritic or dysfunctional joint surface is replaced with something better or by remodeling or realigning the joint by osteotomy or some other procedure. These procedures are also characterized by relatively long recovery times and are highly invasive procedures.

The currently available therapies are not condro-protective. Previously, a popular form of arthroplasty was interpositional arthroplasty with interposition of some other tissue like skin, muscle or tendon to keep inflammatory surfaces apart or excisional arthroplasty in which the joint surface and bone was removed leaving scar tissue to fill in the gap. Other forms of arthroplasty include resection(al) arthroplasty, resurfacing arthroplasty, mold arthroplasty, cup arthroplasty, silicone replacement arthroplasty, etc.

Osteotomy is a related arthroplasty procedure involving cutting of bone to improve alignment. The goal of osteotomy is to relieve pain by changing the anatomy and equalizing forces across the joint. This procedure is often used in younger, more active or heavier patients. Hip osteotomy involves removing bone from the femoral head or from the acetabulum of the hip joint and moving the bones slightly within the joint. This changes the position of the bones of the hip joint to shift the brunt of the patient's weight from damaged joint surfaces to healthier cartilage. A metal plate or pin is inserted to keep the bone in the new position.

Other approaches to treating osteoarthritis involve an analysis of loads which exist at a joint. Both cartilage and bone are living tissues that respond and adapt to the loads they experience. If a joint surface remains unloaded for appreciable periods of time the cartilage tends to soften and weaken. Further, as with most materials that experience structural loads, particularly cyclic structural loads, both bone and cartilage begin to show signs of failure at loads that are below their ultimate strength. However, cartilage and bone have some ability to repair themselves. There is also a level of load at which the skeleton will fail catastrophically. Accordingly, it has been concluded that the treatment of osteoarthritis and other conditions is severely hampered when a surgeon is not able to precisely control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there has been identified a need for devices which facilitate the control of load on a joint undergoing treatment or therapy, to thereby enable use of the joint within a healthy loading zone.

Certain other approaches to treating osteoarthritis contemplate external devices such as braces or fixators which control the motion of the bones at a joint or apply cross-loads at a joint to shift load from one side of the joint to the other. Various of these approaches have had some success in alleviating pain but suffer from lack of patient compliance or lack an ability to facilitate and support the natural motion and function of the diseased joint. Notably, the motion of bones forming a joint can be as distinctive as a finger print, and thus, each individual has his or her own unique set of problems to address. Some prior approaches to treating osteoarthritis have also been remiss in acknowledging all of the basic functions of the various structures of a joint in combination with its unique movement.

Osteoarthritis is the most common type of hip arthritis. As the protective cartilage is worn away by hip arthritis, bare bone is exposed within the joint.

Hip arthritis typically affects patients over 50 years of age. It is more common in people who are overweight, and weight loss tends to reduce the symptoms associated with hip arthritis. There is also a genetic predisposition of this condition, meaning hip arthritis tends to run in families. Other factors that can contribute to developing hip arthritis include traumatic injuries to the hip and fractures to the bone around the joint.

It has been reported that thirty-five percent of all osteoarthritis is found in the hips. In fact, it has been estimated that more than ten million American adults suffer from hip osteoarthritis and more than $6 billion is spent per year treating hip osteoarthritis. Hip osteoarthritis is particularly debilitating. Generally, it is believed that osteoarthritis of the hip is the most disabling of all joint osteoarthritis.

The most common symptoms of hip arthritis are pain with activities, limited range of motion, stiffness of the hip, walking with a limp, and decreased function, strength, activities and quality of life. Hip arthritis symptoms tend to progress as the condition worsens. Interestingly, hip arthritis symptoms do not always progress steadily with time. Often, patents report good months and bad months or symptom changes with weather accurately represent the overall progression of the condition.

Evaluation of a patient hip arthritis should begin with a physical examination and x-rays to determine which course of treatment should be followed. Weight loss is probably one of the most important, yet least commonly performed treatments. The less weight the joint has to carry, the less painful activities will be. Also, limiting certain activities may be necessary, and learning new exercise methods may be helpful. Strengthening of the muscles around the hip joint may help decrease the burden on the hip. Preventing atrophy of the muscles is an important part of maintaining functional use of the hip. Anti-inflammatory pain medications (NSAIDs) are prescription and nonprescription drugs that can help treat pain and inflammation. In more intrusive approaches, hip replacement surgery can hip resurfacing surgery have also been employed to treat hip osteoarthritis. In the most common hip replacement surgery, the cartilage is removed and a metal and plastic ball and socket hip replacement implant is placed in the hip. As an alternative to hip replacement, some patients are opting to pursue hip resurfacing surgery.

However, there is a need for a treatment modality which bridges the gap between the more conservative approaches such as weight loss, physical therapy and anti-inflammatory medicine and a decision to seek major surgical intervention. Such a treatment modality should be minimally invasive yet sufficiently effective to reduce the pain of osteoarthritis. The treatment should also be compatible with hip anatomy taking into consideration the many muscles overlaying the hip joint without hindering motion and avoiding the major arteries and nerves which are present.

SUMMARY

Briefly and in general terms, the present disclosure is directed towards apparatus and methods for treating the hip. Various structures are presented to specifically treat osteoarthritis of the hip joint.

In one aspect, there is disclosed an apparatus for controlling a load on a human hip joint during normal gait while preserving full range of motion. The apparatus includes a rail component for attachment to a pelvis, in which the rail component includes a bearing surface. The apparatus also includes a follower component having a first end and a second end. The first end is connected to a femur and the second end contacts the bearing surface of the rail component during a portion of the normal gait to reduce the load on the human hip joint.

In another aspect, the apparatus for controlling loads includes a rail component having a bearing surface that is attached to a femur. The apparatus also includes a follower component having a first end and a second end. The first end of the follower component is connected to a pelvis, and the second end of the follower component contacts the bearing surface of the rail component during a portion of the normal gait to reduce the load on the human hip joint.

Further, in one embodiment, the apparatus for controlling loads in a hip joint includes a first circular bumper fixed to a first position on a pelvis, and a second circular bumper fixed to a second position on a femur. In this embodiment, the first circular bumper engages the second circular bumper during a portion of the normal gait to reduce the load on the human hip joint.

Other features and advantages of the present disclosure will become apparent from the following detailed description, taken in conjunction with the accompanying drawings, which illustrate, by way of example, the principles of the invention.

BRIEF DESCRIPTION OF THE DRAWINGS

FIGS. 11A-B are perspective views, depicting fourth and fifth embodiments of a load controlling device placed across a hip joint;
FIG. 11C is a perspective view of an alternate linkage between the components of the load controlling device of FIGS. 11A-B.

DETAILED DESCRIPTION

Figure 1:
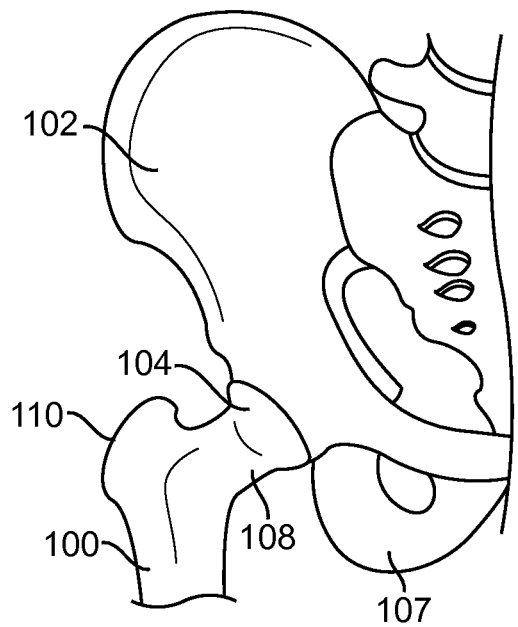
FIG. 1 is a front view, depicting a hip joint.

Referring now to the drawings, which are provided by way of example and not limitation, the present invention is directed towards apparatus and methods for treating the hip joint. The present disclosure seeks to alleviate pain associated with the function of diseased or malaligned members forming the hip joint. Whereas the present disclosure is particularly suited to address issues associated with osteoarthritis, the energy manipulation accomplished by the disclosed apparatus and methods lends itself well to broader applications.

In one particular aspect, the present disclosure seeks to permit and complement the unique articulating motion of the members defining a hip joint of a patient while simultaneously manipulating energy being experienced by both cartilage and osseous tissue (cancellous and cortical bone). Approaches involving varying energy absorption and transfer during the pivoting of the joint and selecting a geometry for the energy absorption assembly to provide necessary flexibility are implemented into various embodiments of the present disclosure. Certain of the embodiments include geometry which accomplishes variable energy absorption designed to minimize and complement the dampening effect and energy absorption provided by the anatomy of the body, such as that found at a hip joint. In certain specific applications, distraction is employed in the energy manipulation approach.

In one particular approach, a bending spring assembly is contemplated to manipulate or absorb forces between body parts. Thus, an assembly utilizing an element or elements which respond to bending or changes in elongation may be desirable to treat afflictions such as osteoarthritis. Certain of the assemblies can incorporate features which insure correct device alignment as the member transitions between compressed and uncompressed states.

With specific reference to FIGS. 1-3C, certain features of typical hip anatomy are presented. The hip joint is a ball-and-socket joint. This arrangement gives the hip a large amount of motion needed for daily activities like running, walking, sitting, and climbing stairs. The deepest layer of the hip includes the bones and the joints. The next layer is made up of the ligaments of the joint capsule. Tendons and the muscles overlay the ligaments and joint capsule.

Figure 2:
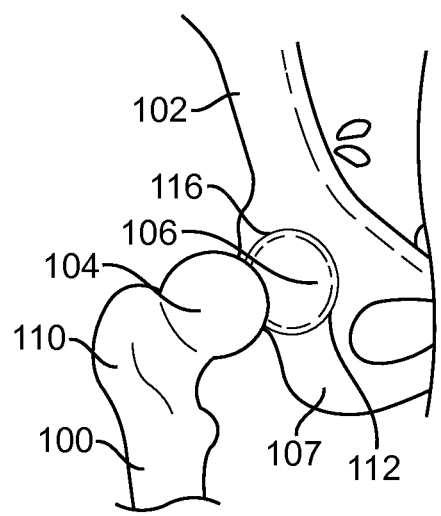
FIG. 2 is a partially exploded and enlarged view, depicting details of the hip joint.

The structures of the hip can be divided into several categories. These include bones and joints, ligaments and tendons, muscles and blood vessels. The bones of the hip are the femur (the thighbone) 100 and the pelvis 102. The top end of the femur is shaped like a ball. This ball is called the femoral head 104. The femoral head 104 fits into a round socket on the side of the pelvis referred to as the acetabulum 106 (FIG. 2). Structure extending below and lateral to the acetabulum 106 is the portion of the pelvis called the ischium 107.

The femoral head 104 is attached to the rest of the femur 100 by a short section of bone called the femoral neck 108. A large bump juts outward from the top of the femur 100, next to the femoral neck 108. This bump, or the greater trochanter 110, can be flat along the side of your hip. Large muscles connect to the greater trochanter 110.

Articular cartilage 112 is the material that covers the ends of the bones of any joint (FIG. 2). Articular cartilage is about one-quarter of an inch thick in the large, weight-bearing joints like the hip. Articular cartilage has a rubbery consistency and is slippery, which allows the joint surfaces to slide against one another without causing damage. The function of articular cartilage is to absorb shock and provide an extremely smooth surface to make motion easier. In the hip, articular cartilage covers the end of the femur 100 and the socket portion of the acetabulum 106 in the pelvis. The cartilage is especially thick in the back part of the socket, as this is where most of the force occurs during walking and running.

Figure 4:
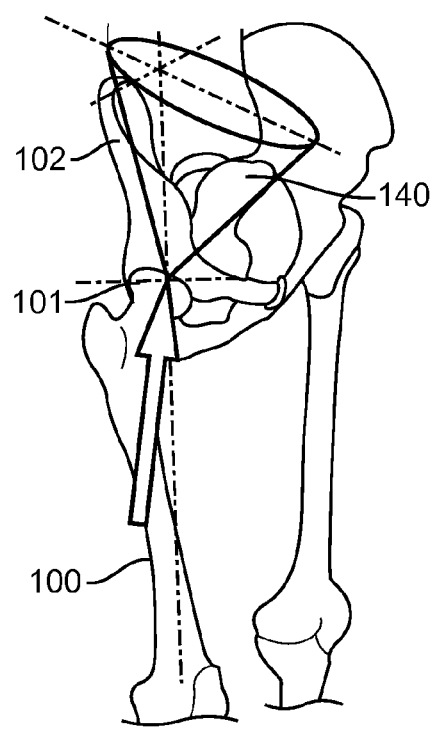
FIG. 4 is a perspective view, depicting angles of forces typically found in a hip joint.

A cone 140 depicted in FIG. 4 exhibits the direction of the majority of forces applied to the hip socket during the gait cycle. A goal of the load controlling apparatus for the hip is to off-load some of these forces while maintaining as much natural motion as is possible. It has been found that moderate cyclic loading on the hip joint is beneficial and necessary to biological health.

There are several ligaments in the hip. Ligaments are soft tissue structures that connect bones to bones. A joint capsule is a watertight sac that surrounds a joint. In the hip, the joint capsule is formed by a group of three ligaments that connect the femoral head to the acetabulum. These ligaments are the main source of stability for the hip and help hold the hip in place. A special type of ligament forms a unique structure inside the hip called the labrum 116 (FIG. 2). The labrum is attached almost completely around the edge of the acetabulum 106. The shape and the way the labrum 116 is attached create a deeper cup for the acetabulum socket. This small rim of cartilage can be injured and cause pain and clicking in the hip.

The hip is surrounded by thick muscles. The gluteals make up the muscles of the buttocks on the back of the hip. The inner thigh is formed by the adductor muscles. The main action of the adductors is to pull the leg inward toward the other leg. The muscles that flex the hip are in front of the hip joint. These include the iliopsoas muscle. This deep muscle begins in the low back and pelvis and connects on the inside edge of the upper femur. Another large hip flexor is the rectus femoris. The rectus femoris is one of the quadriceps muscles, the largest group of muscles on the front of the thigh. Smaller muscles going from the pelvis to the hip help to stabilize and rotate the hip. The load controlling apparatus can be located beneath the muscles and ligaments of the hip or can be positioned between the muscles and tendons.

Figure 3A:
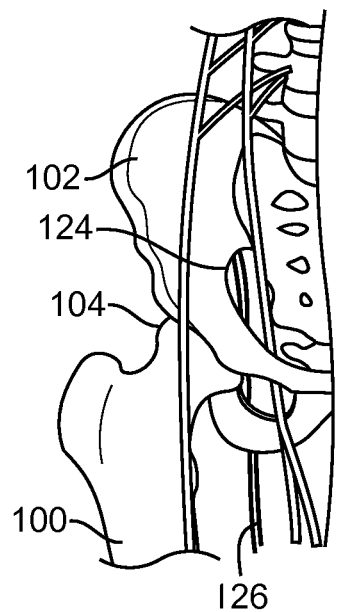
FIGS. 3A and 3B are front views, depicting the arteries and nerves of the hip joint.
Figure 3B:
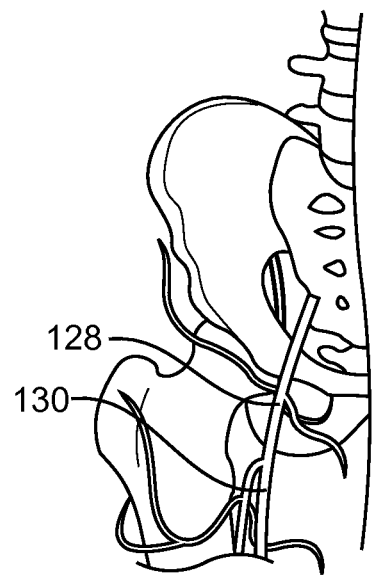

All of the nerves that travel down the thigh pass by the hip (See FIG. 3A). The main nerves are the femoral nerve 124 in front and the sciatic nerve 126 in back of the hip. A smaller nerve, called the obturator nerve (not shown), also goes to the hip. These nerves carry the signals from the brain to the muscles that move the hip. Traveling along with the nerves are the large vessel that supply the lower limb with blood (See FIG. 3B). The large femoral artery 128 begins deep within the pelvis. It passes by the front of the hip area and goes down toward the inner edge of the knee. The femoral artery has a deep branch, called the profunda femoris 130. The profunda femoris sends two vessels that go through the hip joint capsule. These vessels are the main blood supply for the femoral head. Other small vessels form within the pelvis and supply the back portion of the buttocks and hip.

The hip joint has the greatest range of movement of any joint, second only to the shoulder. The full range of motion of the hip is much larger than used in daily routine activities. For example, in flexion and extension this maximum range of motion is 150° and 15° respectively while during normal gait, there is typically only 45° of flexion and 10° of extension. For abduction/adduction, the maximum range of motion is 45°/30° whereas during normal gait, the range of motion is closer to 7°/10°. Further, as to internal/external rotation, the maximum range of motion can be 60°/60° and only 4°/3° during normal gait. Interestingly, however, in patients suffering from hip osteoarthritis normal gate changes and the range of motion increases in some motions and decreases in other motions. That is, flexion/extension or an osteoarthritic hip during walking has been observed to be 25°/18°, abduction/adduction at 4°/7° and internal/external rotation at 10°/7°.

Figure 5:
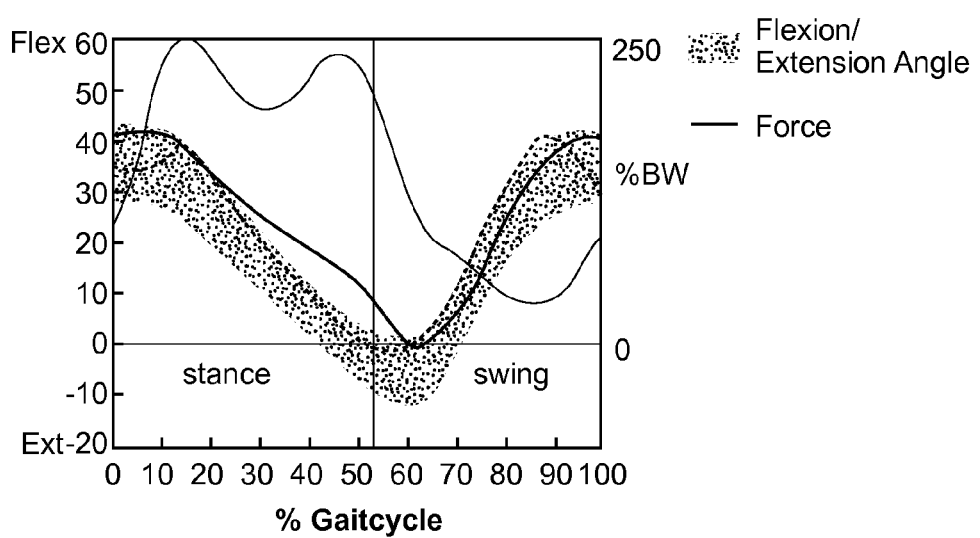
FIG. 5 is a chart, depicting a force and motion relative of a hip joint during gait.

Referring now to FIG. 5, a force-motion relationship of a hip joint during gait is presented. Of particular interest to treatment, it is noted that peaks in load occur between 40° and 10° flexion during the stance portion of the gate cycle. It is further noted that vertical forces dominate in the hip joint. It has also been observed that forces of 2.4 times body weight are common during normal walking. Higher forces of up to about 9 times body weight are observed in the hip when running, stumbling or walking down stairs. Lower forces exist when sitting or standing.

Figure 6:
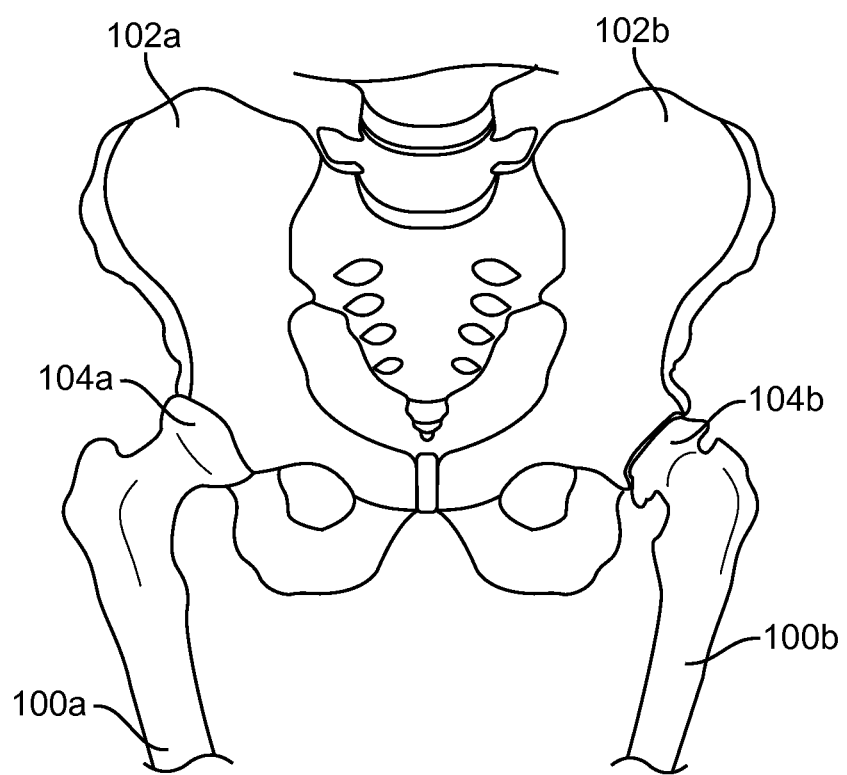
FIG. 6 is a front view, depicting a healthy hip joint and a hip joint suffering from osteoarthritis.

As shown in FIG. 6, showing a healthy hip 102a and an osteoarthritic hip 102b, osteoarthritis can be exhibited as osteophytes and deteriorated cartilage. Often, changes in the femur head 104 and the acetabulum 106 mirror each other or are similar. Various overlapping steps in osteoarthritis include initial articular cartilage degeneration, osteophyte formation in areas of low or no load causing decreases in range of motion and the flattening of the femoral head. Eburnation where bared bone and cartilage are worn away occurs as does necrosis, sclerosis and cyst formation.

Aside from ostephyte formation, osteoarthritis develops primarily in regions of high load. As shown by the schematic cone 140 in FIG. 4, the majority of forces in the hip joint are through anterior, superior and medial regions of the femoral head 104. Thus, devices for manipulating such loads are contemplated to fight the degeneration of the hip joint.

The load manipulation devices of the present disclosure are contemplated to be placed across a hip joint. Fixation structures for fixing the load manipulation structures to the bone may be attached, for example, to the femur and pelvis. These are linked together with an absorber, the linking structure being configured to accommodate natural motions of the hip joint. The absorber is designed to absorb or off-load some portion of the load normally carried by the hip joint. The device itself is positioned such that the resultant force/unloading vector corresponds to a desired direction of off-loading. In particular, unloading is contemplated to occur in directions relating to the force cone 140. It is also contemplated that multiple load manipulation devices can be placed at various locations across the hip joint to thereby balance out and/or decrease moment forces being accommodated.

In various approaches, on the femur side of a hip joint, the load manipulation devices can be attached at inferior and superior positions, to the greater trochanter, the lesser trochanter, at ostephytes on the femur, or along a bend in the neck of the femur. The device can also be affixed all around the neck and head of the femur including the base and underside of the femur head. Also, it is contemplated that on the femur side, the fixation point be beneath, within, above or in place of muscle. On the pelvis side, fixation of the absorber can be at the top or bottom of the acetabulum, along a ridge defining the acetabulum or along surrounding areas. Additionally, various surfaces on and around the ischium are also contemplated for fixation. Muscle may need to be displaced to gain sufficient access to the ischium to effect a proper fixation.

With reference now to FIGS. 7-16, there is shown various embodiments of load manipulation assembly implanted across a hip joint. Generally, the load manipulation assembly includes a rail component and a follower component. In some embodiments, the rail component and/or the follower component include one or more springs, absorbers, unloaders or actuators to absorb or off-load forces on the hip joint. Alternatively, the rail and/or follower components may be made from flexible materials and/or one or more materials having different physical properties. The follower component moves relative to the rail component during a gait cycle and absorbs or off-loads some portion of the load normally carried by the hip joint. In some embodiments, the follower and rail components are in contact with one another throughout the gait cycle. Alternatively, the follower and rail components are only engaged for a portion of the gait cycle.

Figure 7A:
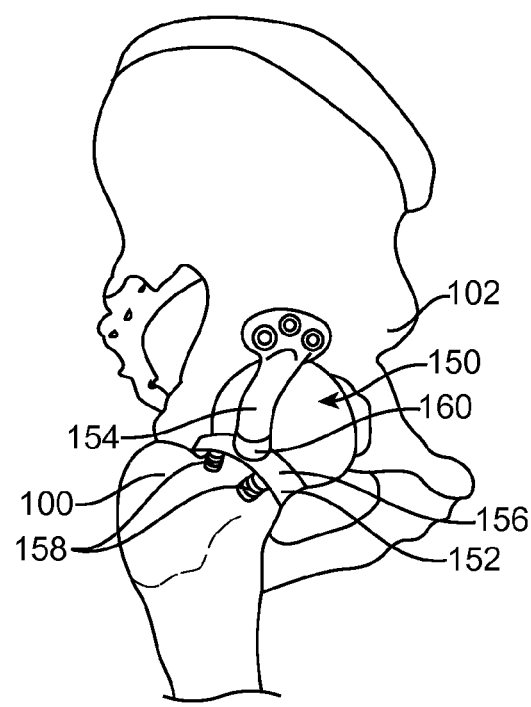
FIG. 7A is a side view, depicting a first embodiment of a load controlling device placed across a hip joint.
Figure 7B:
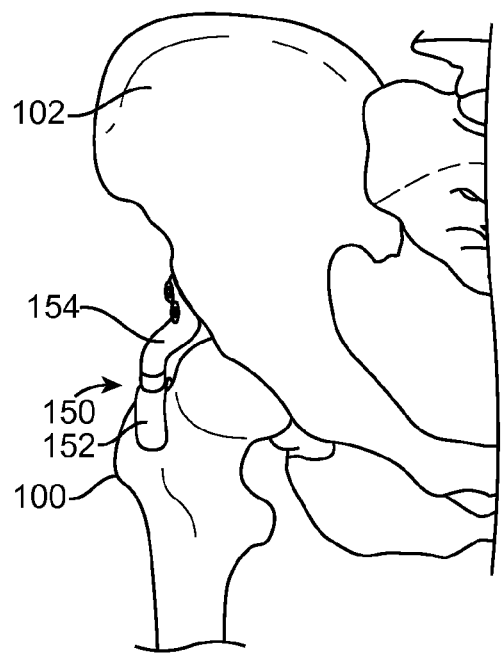
FIG. 7B is a front view of the embodiment of FIG. 7A.

FIGS. 7A-7B illustrate one embodiment of a load manipulation assembly 150 in which the rail component 152 is fixed to the femur 100 and the follower component 154 is fixed to the pelvis 102. As shown in FIGS. 7A-7B, the rail component 152 is attached about the neck of the femur 100 to the medial and anterior surfaces of the neck. In alternate embodiments, the rail component 152 can be attached to the greater trochanter, the lateral cortex of the femur 100, the distal surface of the femur neck or to combinations of these.

The rail component 152 is generally arch shape with a top surface 156 (also referred to as a bearing surface) that engages the follower component 154. As shown in FIGS. 7A-7B, the bearing surface 156 is in the shape of a flat arch shaped band. That is, a flat surface is a surface having no elevation change when moving across the bearing surface from one edge to an opposite edge of the bearing surface. In other embodiments, the top surface 156 can be convex, concave, or grooved in other embodiments.

The shape of the arch of the top surface 156 may be shaped or configured to maximize unloading of the hip joint during various positions of a gait cycle. For example, an arch shape with a high medial portion will maximize unloading when the hip is at a neutral or standing position.

As shown in FIG. 7A, two spring elements 158 engage the base of the rail component 152 and connect the rail component to the femur 100. The spring elements 158 can furnish the flexibility and force-carrying capacity of the rail 152. Alternatively, the rail component 152 is made from a flexible material, such as a resilient material or a spring material, to provide these characteristics. In other embodiments, the rail component 152 can be directly fixed to the bone. Although two spring elements 158 have been shown, any number of spring elements may be provided between the rail component 152 and the bone surface to which the rail is attached. In one embodiment, each of the spring elements 158 are separately attached to the bone by one or more fasteners or bone screws. In another embodiment, a base member (not shown) is secured to the bone and the spring elements 158 are movable thereon.

The follower component 154 is fixed to the pelvis 102, for example, the acetabelum with one or more locking screws. The follower component 154 is shaped to avoid certain bone structures and in combination with the rail component 152 to absorb or off-load forces on the hip joint. The distal end 160 of the follower component 154 may be shaped (e.g., rounded) to allow the follower component to move freely with respect to the rail component 152, as shown in FIGS. 7A-7B. Alternatively, one or more balls, rollers, or wheels 160 are provided at the distal end of the follower component 154 to facilitate movement over the top surface 156 of the rail component 152. The bearing surface 156 of the rail component 152 may be contoured, i.e. concave, to correspond in shape to the distal end 160 of the follower component 154. In some embodiments, the follower component 154 and/or the rail component 152 may be finished, polished, coated or made from materials to facilitate movement of the follower component 154 relative to the rail component 152 during the gait cycle and/or which reduce wear.

Figure 8:
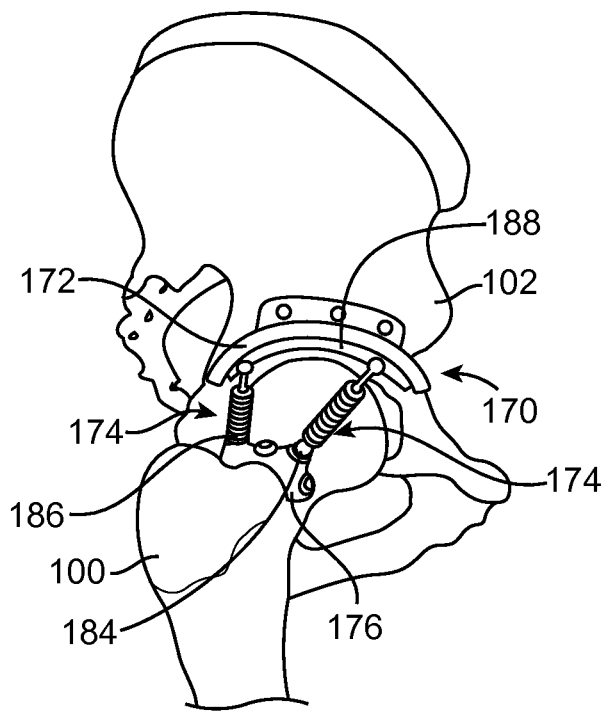
FIG. 8 is a side view, depicting a second embodiment of a load controlling device placed across a hip joint.

FIG. 8 illustrates another embodiment of a load manipulation assembly 170 in which a rail component 172 is fixed to the pelvis 102, and two follower components 174 are coupled to the femur 100 via a base 176. The rail component 172 is fixed to the pelvis by bone screws and is formed in an arc shape which generally follows the cure of the superior edge of the acetabular cup. While FIG. 8 shows a load manipulation assembly 170 having two follower components 174, any number of follower components may be used with the rail component 172.

Figure 8A:
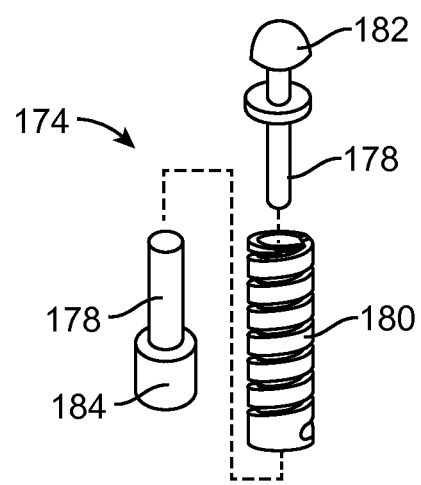
FIG. 8A is an exploded view of one embodiment of a follower component used in the load controlling device of FIG. 8.

In one embodiment, the follower component 154 in FIG. 8 includes an arbor/piston 178 surrounded by a spring 180, as shown in FIG. 8A. Alternatively, the load absorbing arm can include other flexible elements such as, but not limited to, polymers, resilient materials, gas/fluid pistons, or any combination thereof. A ball 182 is provided at one end of the follower component 174. The ball 182 engages the rail component 172. In one embodiment, the rail component includes a partially enclosed track and the ball 182 is captured by and slides within the track. Alternatively, the ball contacts 182 the rail component 172 for at least a portion of the gait cycle. In other embodiments, the ball 182 may be replaced with a wheel, bearing, or other rotating or non-rotating device. The end 184 of the follower component 174 that is opposite the ball 182 engages and is secured to a base component 176. In other embodiments, the end 184 of the follower component 174 can include a ball, socket, ridge, groove, recess, or is otherwise shaped to engage the base component 176 in a movable manner.

As shown in FIG. 8, the base component 176 includes two openings 186 that receive the ends 184 of the follower component 174. The openings 186 on the base component 176 and the ends of the follower component 174 may be a ball and socket connection. Alternatively, the connection between the base component 176 and the follower component 174 may be any pivoting connection known or developed in the art.

The rail and base components 172, 176 can be fixed to the bones with locking screws or other attachment means known or developed in the art. As shown in FIG. 8, the base component 176 is fixed to the medial and anterior neck of the femur 100. Alternatively, the base component 176 can be fixed on the lateral cortex of the femur 100, the greater trochanter or on the posterior surfaces of the neck of the femur.

The rail component 172 has a surface 188 that interacts with a portion the follower components 174. In one embodiment, the surface 188 of the rail component 172 may be shaped (e.g., concave or have a track or groove) to capture a portion of the follower components 174. That is, the follower component 174 is shaped so that the follower component is not easily removed from the rail component 172.

Figure 9:
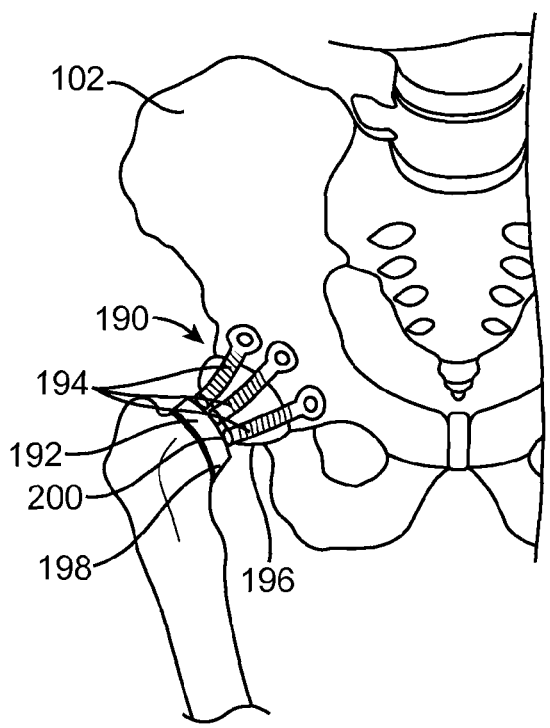
FIG. 9 is a front view, depicting a third embodiment of a load controlling device placed across a hip joint.

FIG. 9 illustrates another embodiment of a load manipulation assembly 190. The load manipulation assembly 190 includes a rail member 192 fixed to the neck of the femur 100 with bone fixators such as, but not limited to, locking screws. The rail 192 includes a flat bearing surface 200 as shown in FIG. 9. Alternatively, the rail 192 has a cam-like surface (not shown) having raised and/or lowered areas to provide varying resistance as the follower members 194 move along the top surface 200 of the rail 192. As shown in FIG. 9, three follower members 194 are mounted to the pelvis 102 via fixation screws at locations spaced around the acetabular cup. However, other numbers of followers may also be used and their position can be selected depending on the particular disease and anatomy of a patient being treated.

The follower members 194 include a spring 196 supported on a rigid, telescoping piston arrangement that allows the follower member to extend and compress without bending while transferring forces from the hip to the femur. The follower members 194 also include a rotating component 198 such as, but not limited to, wheel, roller, bearing or other component that is able to rotate about a fixed axle and/or axis. The rotating component 198 contacts the surface 200 of the rail 192 during one or more portions of a gait cycle. In one embodiment, the loading members may have the same structure as the follower member shown in FIG. 8A. Forces on the hip joint may be unloaded during the gait cycle as the follower member moves along (and pushes against) the rail surface 200.

While the follower member 194 in FIG. 9 is illustrated with a single spring 196, multiple springs may be used to provide load bypass or absorption. Additional absorber designs which may be used in place of the follower member 194 are shown in U.S. Published Patent Application No. 2008/275558, which is incorporated herein by reference in its entirety.

Figure 10:
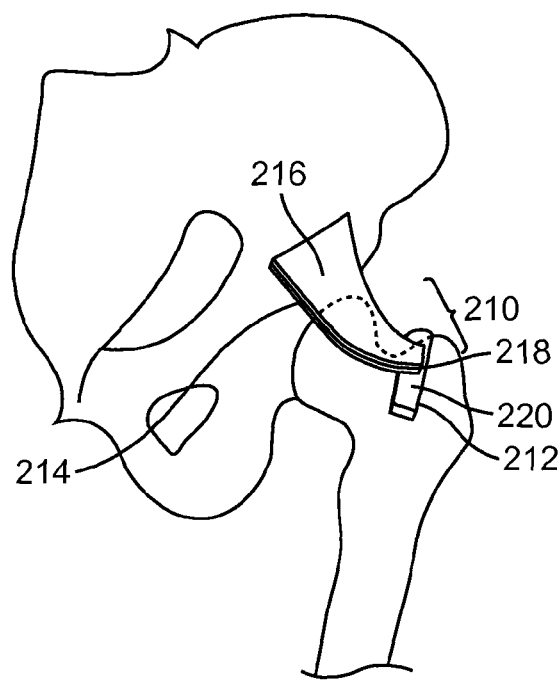
FIG. 10 is a front view, depicting a fourth embodiment of a load controlling device placed across a hip joint.

FIG. 10 illustrates yet another embodiment of a load manipulation assembly 210 having a rail member 212 fixed to the femur and a follower member 214 fixed to the pelvis. In an alternate embodiment, the rail member 212 may be fixed to the pelvis and the follower member 214 is coupled to the femur. The rail member 212 is secured on the neck of the femur or the greater trochanter adjacent the neck. The rail member 212 includes a superior or superior and medially oriented surface 220 that is generally flat as shown in FIG. 10. Alternatively, the rail 212 may have a cam-like surface (not shown) having raised and/or lowered areas to provide varying unloading of the hip joint as the follower member 214 moves along the top surface.

As shown in FIG. 10, the follower member 214 is coupled to the pelvis by one or more fasteners (not shown). The follower member 214 includes a body 216 having a bearing surface 218 and is either in the form of a flexible leaf spring or is generally rigid. The body is shaped to avoid the anatomy in the hip. In yet another embodiment, a portion of body 216 is flexible and a portion is rigid, which allows the body to be flexible to a certain degree. In various embodiments, the body 216 may be entirely rigid or it can be flexible. Alternatively, the body 216 can be rigid with flexible portions, or vice versa. The bearing surface 218 of the body 216 contacts the top surface 220 of the rail member 212. The bearing surface 218 can be finished, polished, coated or made from materials to facilitate movement of the follower member relative to the rail member during the gait cycle. In alternate embodiments, the bearing surface 218 may include one or more rotating members to facilitate movement of the follower member 214 over the top surface 220 of the rail member 212. The follower member 214 can contact the top surface 220 of the rail member 212 during the entire gait cycle or only a portion thereof.

FIGS. 11A-C show two embodiments of a load manipulation assembly 220 having an arc shaped rigid loop 222 (e.g., wire or band) fixed to the femur 100. As shown in FIG. 11, a follower member 224 includes a rigid bar 226 having an opening 228 at one end. The loop 222 passes through the opening 228 of the rigid bar 226 to link the rigid loop and the follower member 224 together. Additionally, the rigid bar 226 is able to slide along the rigid loop 222 during motion of the hip joint to partially or fully unload the hip joint during some or all of the hip motion. In another embodiment, the rigid bar 226 can be coupled to the rigid loop 222 by a ball and socket joint 231 (or ball and track) as shown in FIG. 11C.

Opposite the opening 228, the rigid bar 226 may be coupled to the pelvis 102 via a base. The rigid bar 226 can be coupled to the base in a fixed or a movable manner, such as by a ball and socket joint. In one embodiment, the ball is provided at the end of the rigid bar 226 and the socket is provided on a base that is mounted to the pelvis. Alternatively, the socket is provided on the end of the rigid bar and the ball is provided on the base. In another embodiment, a pivot joint can be used to mount the rigid bar 226 to the pelvis 102. In the embodiment, depicted in FIGS. 11A-C, pressure against the rigid loop 222 transmits load from the hip to the femur and functions to at least partially unload the hip joint. The load manipulation assembly 220 may support sufficient forces in some embodiments to move the head of the femur 100 slightly out of the acetabulum. The rigidity and/or flexibility of the loop may be varied in order to vary the force off-loaded from the hip joint. Optionally, the length and rigidity of the bars 226 can also be varied to further cause the load manipulation assembly 220 to be active in a specific loading or motion range.

FIG. 11B illustrates another embodiment of the load manipulation assembly 220 having two follower members 230 coupled to the rigid loop 222. In other embodiments, there can be more than two follower members slidingly coupled to the rigid loop 222. For example, there may be four follower members (not shown) spaced around the rigid loop 222. As shown in FIG. 11B, the follower members 230 include a spring 196 supported on a rigid, telescoping piston arrangement that allows the follower member to extend and compress without bending. The spring 196 can be supported on a rigid telescoping piston arrangement which allows the absorber to extend and compress without bending. Although the absorber 230 is illustrated with a single spring 196, multiple springs may be used to provide load absorption. Additional examples of absorber designs which may be used in place of the absorber 230 are shown in U.S. Published Patent Application No. 2008/0275558, which is incorporated herein by reference in its entirety.

FIG. 11C illustrates another embodiment of a load manipulation assembly 220 having a ball-socket 232 connection between the rigid loop 222 and an absorption member 230.

Figure 12:
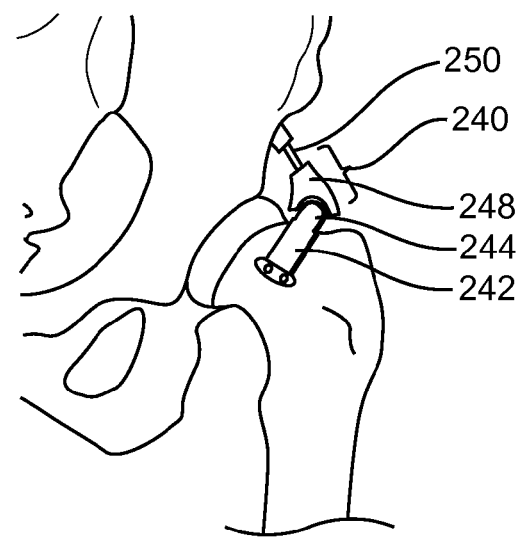
FIG. 12 is a front view, depicting a sixth embodiment of a load controlling device placed across a hip joint.

FIG. 12 illustrates a load manipulation assembly 240 in which the rail assembly 242 includes a raised surface 244 that engages a follower member assembly 246 of the load absorption assembly. The follower assembly 246 can be directly or indirectly coupled to the pelvis. Alternatively, the follower assembly 246 can be anchored within the pelvis. The follower assembly 246 includes a spacer element 250 to adjust the position of the end of the follower assembly 246 that engages the rail assembly 240. In one embodiment, the spacer element 250 is adjustable (i.e., the spacer may be shortened or lengthened). Alternatively, the spacer element (not shown) has a fixed length and shape, but the spacer element may be swapped out for other spacer elements having different lengths and/or shapes.

As shown in FIG. 12, the end 248 of the follower assembly 246 is concave and the rail assembly 242 has a convex surface 244. Alternatively, the end of the follower assembly 246 is convex and the rail assembly has a concave surface. In yet another embodiment, the rail assembly (not shown) may be configured to capture the end 248 of the follower assembly 246, as in a track. The mating surfaces between the follower assembly 246 and rail assembly 242 can be shaped to provide different points of contact or different amounts of load transfer during different phases of the gait cycle.

Figure 13:
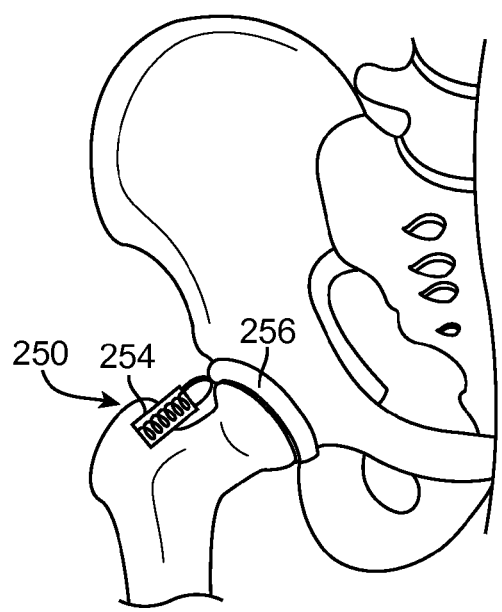
FIG. 13 is a front view, depicting a seventh embodiment of a load controlling device placed across a hip joint.

FIG. 13 illustrates another embodiment of a load manipulation assembly 250 in which the follower assembly 252 is anchored within the pelvis. The load absorption assembly may include a spring 254 or other force transmission device to push the follower assembly 252 into to the bearing surface 258 of the rail member 256. In one embodiment, the spring is placed within or partially within a bore formed in the pelvis, preferably superior of the acetabular cup. In another embodiment, the spring is attached to the end of the load absorption assembly.

Figure 14A:
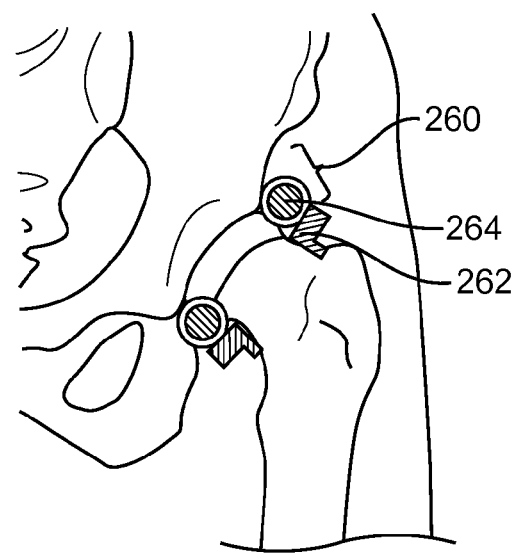
FIGS. 14A-14B are front views, depicting eighth and ninth embodiments of a load controlling device placed across a hip joint.
Figure 14B:
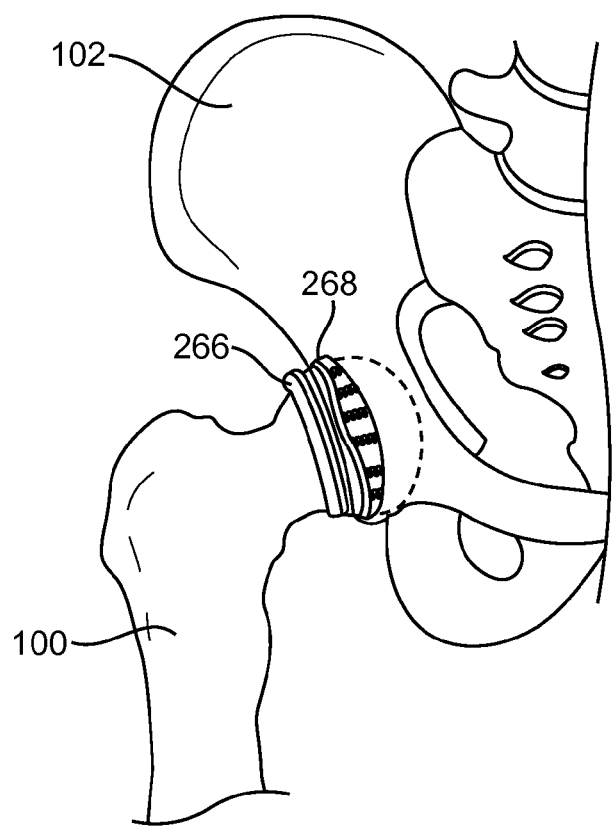

FIG. 14A illustrates yet another load manipulation assembly 260 in which the rail assembly 262 is fixed to and entirely surrounds the neck of the femur. The follower component 264 is a circular bumper that spans the space between the rail assembly 262 and the ilium. The follower 264 and the rail 262 may be continuous or discontinuous. FIG. 14B illustrates another embodiment in which circular bumpers 266, 268 are provided on femur and the acetabulum. The circular bumpers 266, 268 can include a plurality of internal springs or a resilient material which provide compliance to the system. The thickness and/or durometer of the material of the bumpers (e.g., a portion of the bumper and/or entire bumper) can be varied to tailor the follower of the hip joint and/or avoid the anatomy adjacent/surrounding the rail assembly.

To implant the load manipulating assemblies, conventional surgical or minimally invasive approaches can be taken to gain access to a body joint or other anatomy requiring attention. Arthroscopic approaches are contemplated when reasonable to both implant the energy manipulation assembly as well as to accomplish adjusting an implanted assembly. Biologically inert materials of various kinds can be employed in constructing the energy manipulation assemblies of the present invention. The materials can include titanium or titanium alloy, cobalt chromium alloy, ceramic, high strength plastic such as polyetheretherketone (PEEK) or other durable materials. Combinations of materials can also be used to maximize the properties of materials for different parts of the device. At the wear surfaces, the material may include a combination of metal-on-poly, metal-on-metal, metal-on-ceramic or other combinations to minimize wear.

In one embodiment, the various elements can be comprised of silicone, silicone ePTFE, or other elastomeric materials which permit lengthening but resist compression beyond a given amount. Soft and hard segments can be disbursed along the elastomeric absorber to provide the desired compression and lengthening. On compression beyond a neutral position of the absorber, the hard segments provide resistance to compression and restrains the soft sections. The lengthening as well as flexibility of the absorber elements and the positioning of the rails is set such that the full or nearly full range of motion of a hip joint is maintained. Although the rail and follower elements are shown arranged primarily on the anterior and superior surfaces of the hip joint, they can also be arranged on the posterior, medial and lateral sides of the hip joint. They can be at converging or diverging angles with respect to one another or crossing arrangements.

As with each of the disclosed embodiments, a plurality of load controlling devices can be positioned across a hip joint. For this and other embodiments, the fixation points of the device are contemplated to be outside of the hip capsule and the absorber is positioned along natural planes and lines of the hip ligaments and away from major arteries and nerves. On the femur side, fixation of terminal ends of the load controlling device can for example, be configured to be placed along the greater trochanter and the neck of the femur.

It is to be borne in mind that each of the disclosed various structures can be interchangeable with or substituted for other structures. Thus, aspects of each of the assemblies can be employed across approaches. Moreover, the various manners of engaging energy absorbing structures, rails, followers with attachment structures and attachment structures to body anatomy can be utilized in each approach. Also, one or more of the various disclosed assemblies can be placed near a treatment site and at various angles with respect thereto. Pressure sensing and drug delivery approaches can also be implemented in each of the various disclosed embodiments.

Certain components of most embodiments can be designed for easy removal and, if necessary replacement while others are intended for permanent fixation. The devices can also be implanted encased within a sheath. The permanent components are fixation components which can have bony in-growth promoting surfaces and are responsible for fixation of the system to the skeletal structure. The removable components include the mobile elements of the system such as the link members and/or the pivots or ball joints.

The disclosed embodiments permit the exchange of key components of the system due to device failure, patient condition change or newer improved systems being available. Additionally if the patient subsequently requires further surgery the links may be removed to facilitate the additional procedure.

Further, certain of the contemplated mechanisms can be made to be completely disengaged mechanically and then brought into action under various conditions and during certain phases of the gait cycle. This discontinuous functionality—and the ability to tune that functionality to a particular patient's gait or pain is consequently a feature of one or more of the disclosed embodiments.

Location of the permanent fixation components is important to fixation strength, ability to complete subsequent procedures, and location of pivots or ball joints. The fixation strength of the system, and therefore load bearing capacity, is dependent on the integrity of the bone onto which the plate is fixed. To ensure strong fixation, in one embodiment, the fixation components span along the cortical bone and cancellous (or trabecular) bone. The system may utilize fixation on two cortical surfaces using through pins or bicortical screws.

A common joint procedure is joint replacement as previously described. The procedure of replacing a diseased joint includes resection of the surfaces of the joint and replacement with synthetic materials. To enable implantation of the energy absorbing system without impacting the potential to complete subsequent procedures (e.g., joint replacement) the permanent fixation components in a preferred embodiment are positioned at a location that does not compromise the total joint zone.

Many articulating joints are not simply pivot joints but involve complex multi-axis rotation and translation movements. To achieve its intended purpose, the energy absorber must accommodate these movements but also absorb and transfer energy during the required range of motion. To do so the joints on the device may be either located at points on the bones of least motion, or the joint mechanism must incorporate motion beyond simple uni-axial rotation or a combination of both.

Further, the fixation components can be positioned such that they orientate the attached device joint locations to preferred locations described by minimal or known motion characteristics. The device joint locations may be finely adjusted within a defined region on the fixation component to further optimize the device joint location. The device joint mechanism can also be configured to accommodate the positional changes and therefore can be placed on any distal point on the fixation component.

Therefore, the present invention provides a number of ways to treat body tissues and in particular, to absorb energy or manipulate forces to reduce pain. The disclosed devices can be used throughout the body but have clear applications to articulating body structures such as joints.

Thus, it will be apparent from the foregoing that, while particular forms of the invention have been illustrated and described, various modifications can be made without parting from the spirit and scope of the invention.

We claim:

1. An apparatus for controlling a load on a human hip joint during normal gait while preserving motion, the apparatus comprising:
   a rail component for attachment to a pelvis, the rail component including a bearing surface; and
   two follower components, each having a first end and a second end, each first end configured to be connected to a femur and each second end contacting the bearing surface of the rail component during a portion of the normal gait to reduce the load on the human hip joint;
   wherein the bearing surface of the rail has a length and a width and wherein the length is larger than the width;
   wherein the follower components are moveable relative to the rail along the length of the bearing surface;
   wherein the bearing surface is shaped to capture the second end of each follower component such that the second end of each follower component is not separable from the bearing surface.

2. The apparatus of claim 1, wherein the bearing surface is contoured.

3. The apparatus of claim 1, wherein the first end of each follower component is configured to be connected to the femur via a base assembly.

4. The apparatus of claim 1, wherein each follower component comprises a compression element and a piston and arbor assembly, configured to unload the hip joint by compression of the compression element, and wherein the piston and arbor assembly extends to allow near natural motion of the hip joint.

5. The apparatus of claim 1, wherein the second end of each follower component includes a rotating member contacting the bearing surface of the rail component.

6. The apparatus of claim 1, wherein the rail component is configured to be mounted along a portion of an acetabulum of the femur.

7. An apparatus for controlling a load on a human hip joint during normal gait while preserving motion, the apparatus comprising:
   a rail component for attachment to a femur, the rail component having a bearing surface and two opposite ends;
   two follower components, each having a first end and a second end, each first end configured to be connected to a pelvis and each second end contacting the bearing surface of the rail component during a portion of the normal gait to reduce the load on the human hip joint;
   wherein each follower component is configured to translate along the rail and rotate with respect to the rail; and
   wherein the bearing surface is shaped to capture the second end of each follower component such that the second end of each follower component is not separable from the bearing surface.

8. The apparatus of claim 7, further comprising one or more springs configured to be positioned between the rail component and the femur, the one or more springs counteracting natural compressive forces experienced by the hip joint during normal gait.

9. The apparatus of claim 7, wherein the first end of each follower component is configured to be connected to the pelvis via a base assembly.

10. The apparatus of claim 7, wherein the bearing surface and the second end of each follower component are mutually configured so that the follower translates along the rail along a path extending between the ends of the rail.

11. The apparatus of claim 7, wherein the bearing surface is contoured.

12. The apparatus of claim 7, wherein the second end of each follower component includes a rotating member, wherein the rotating member contacts the bearing surface of the rail component.

13. The apparatus of claim 7, wherein each follower component comprises a compression element and a piston and arbor assembly, configured to unload the hip joint by compression of the compression element, and wherein the piston and arbor assembly extends to allow near natural motion of the hip joint.

14. The apparatus of claim 7, wherein each follower component comprises an elastomeric element which stiffens in compression, is bendable and capable of elongation.

15. The apparatus of claim 7, wherein each follower component comprises a leaf spring.

16. The apparatus of claim 7, wherein the rail assembly comprises a loop having a first end and a second end configured to be fixed to the femur.

* * * * *